(12) United States Patent
Hayashi et al.

(10) Patent No.: US 10,234,469 B2
(45) Date of Patent: Mar. 19, 2019

(54) BLOOD STATE ANALYSIS DEVICE, BLOOD STATE ANALYSIS SYSTEM, BLOOD STATE ANALYSIS METHOD, AND STORAGE DEVICE

(71) Applicant: Sony Corporation, Tokyo (JP)

(72) Inventors: Yoshihito Hayashi, Chiba (JP); Marcaurele Brun, Tokyo (JP); Kenzo Machida, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 15/302,914

(22) PCT Filed: Apr. 9, 2015

(86) PCT No.: PCT/JP2015/001989
§ 371 (c)(1),
(2) Date: Oct. 7, 2016

(87) PCT Pub. No.: WO2015/159516
PCT Pub. Date: Oct. 22, 2015

(65) Prior Publication Data
US 2017/0030934 A1  Feb. 2, 2017

(30) Foreign Application Priority Data
Apr. 17, 2014 (JP) ................ 2014-085511

(51) Int. Cl.
*G01N 33/86* (2006.01)
*G01N 33/49* (2006.01)

(52) U.S. Cl.
CPC ........... *G01N 33/86* (2013.01); *G01N 33/491* (2013.01); *G01N 33/4905* (2013.01)

(58) Field of Classification Search
CPC ..................................................... G01N 33/86
USPC ....................................................... 702/19
See application file for complete search history.

(56) References Cited

U.S. PATENT DOCUMENTS

| | | | |
|---|---|---|---|
| 5,686,309 A | 11/1997 | Frank et al. | |
| 2010/0292932 A1 | 11/2010 | Won | |
| 2012/0035450 A1 | 2/2012 | Hayashi | |
| 2014/0014509 A1 | 1/2014 | Yan et al. | |
| 2016/0018346 A1 | 1/2016 | Hayashi et al. | |
| 2017/0023597 A1 | 1/2017 | Hayashi et al. | |

FOREIGN PATENT DOCUMENTS

| | | |
|---|---|---|
| CN | 1914511 A | 2/2007 |
| CN | 101542292 A | 9/2009 |
| CN | 101784294 A | 7/2010 |
| CN | 102099683 A | 6/2011 |
| CN | 102768179 A | 11/2012 |
| CN | 103471980 A | 12/2013 |
| EP | 1 862 792 A2 | 12/2007 |
| EP | 2 098 867 A2 | 9/2009 |
| EP | 2348319 A1 | 7/2011 |
| EP | 3133390 A1 | 2/2017 |
| GB | 2260407 A | 4/1993 |
| JP | 10-123140 A | 5/1998 |
| JP | 2000-503772 A | 3/2000 |
| JP | 2002-542452 A | 12/2002 |
| JP | 2009-243955 A | 10/2009 |
| JP | 2010-181400 A | 8/2010 |
| JP | 2012-147451 A1 | 7/2014 |
| WO | WO 99/47907 A1 | 9/1999 |
| WO | WO 2005/054847 A1 | 6/2005 |
| WO | WO 2006/129703 A1 | 12/2006 |
| WO | WO 2011/159820 A1 | 12/2011 |
| WO | WO 2013/067536 A1 | 5/2013 |
| WO | WO 2013/153735 A1 | 10/2013 |
| WO | WO 2014/036484 A1 | 3/2014 |
| WO | WO 2015/159516 A1 | 10/2015 |

OTHER PUBLICATIONS

Hayashi et al., The effects of erythrocyte deformability upon hematocrit assessed by the conductance method, Physics in Medicine and Biology, 54 (2009), 2395-2405.
Irimajiri et al., Zenketsu no Yuden Kyodo kara Mita Sekkekkyu Gyoshu (Renzen Keisei, Biotechnology, 2000, vol. 78, No. 5, pp. 162-165.
Extended European Search Report dated Sep. 22, 2017 in connection with European Application No. 15779518.8.
International Preliminary Report on Patentability dated Oct. 27, 2016 in connection with International Application No. PCT/JP2015/001989.
Chinese Office Action dated Jul. 11, 2018 in connection with Chinese Application No. 2015800188598, and English translation thereof.
Communication pursuant to Article 94(3) dated May 15, 2018 in connection with EP 15779518.8.
Chinese Office Action dated Jul. 20, 2018 in connect with Chinese Application No. 2015800190193 and English translation thereof.
Japanese Office Action dated Apr. 10, 2018 in connection with Japanese Application No. 2014-085511, and English translation thereof.
Atsuko Narita et al., Error factor in blood clotting inspection, first report, influence caused by specimen extraction method, medical inspection, 1995, vol. 44(5), 890-894.

*Primary Examiner* — Jerry Lin
(74) *Attorney, Agent, or Firm* — Wolf, Greenfield & Sacks, P.C.

(57) ABSTRACT

A blood state analysis device (1) that analyzes a state of a blood sample, as used for clotting time testing, said blood sample comprising a plasma and at least one reagent, including a correction unit (11) configured to correct a measured blood coagulation evaluation result of the blood sample based on a relation between reference concentrations of the at least one reagent in plasma and reference blood coagulation evaluation results, the at least one reagent is an anticoagulation treatment releasing agent, a coagulation activator, an anticoagulant, a platelet activator, an antiplatelet drug, or a combination thereof and is present in the blood sample. For instance, such device (1) allows to correct blood clotting time results with respect to concentrations of an anti-coagulant drug present in the blood sample.

20 Claims, 8 Drawing Sheets

[Fig. 1]
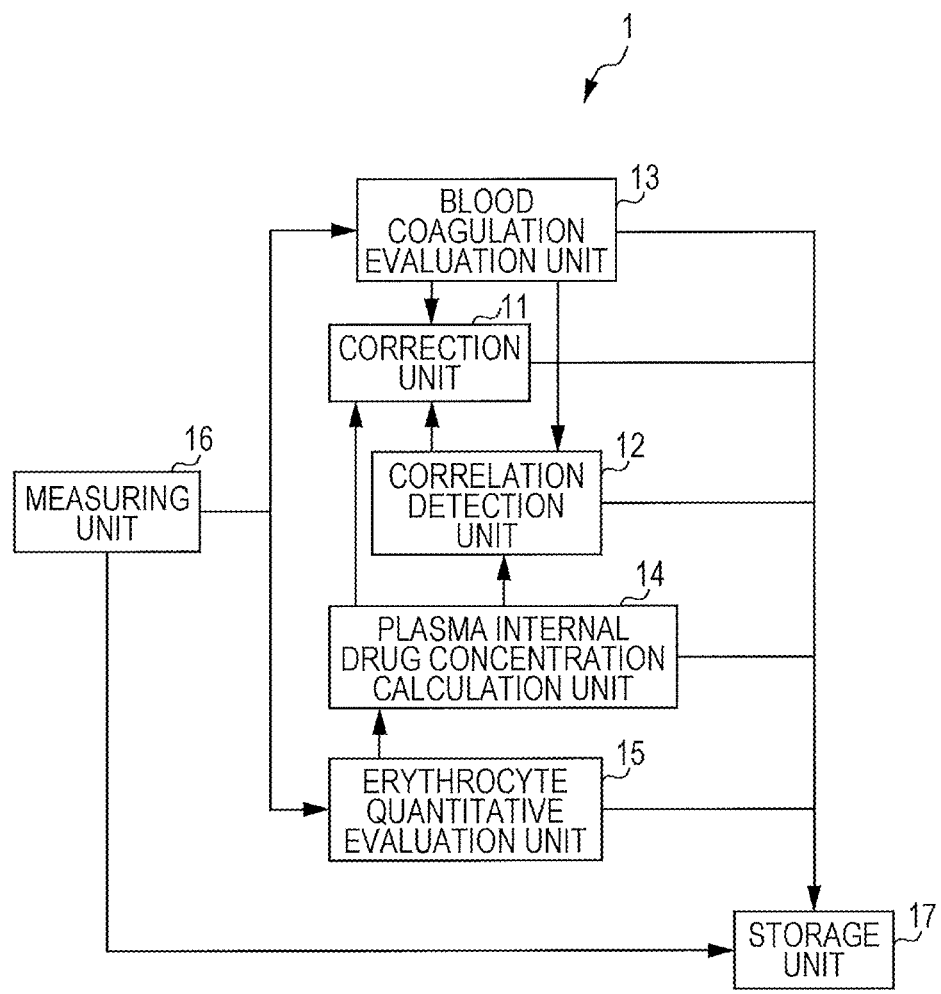

[Fig. 2]
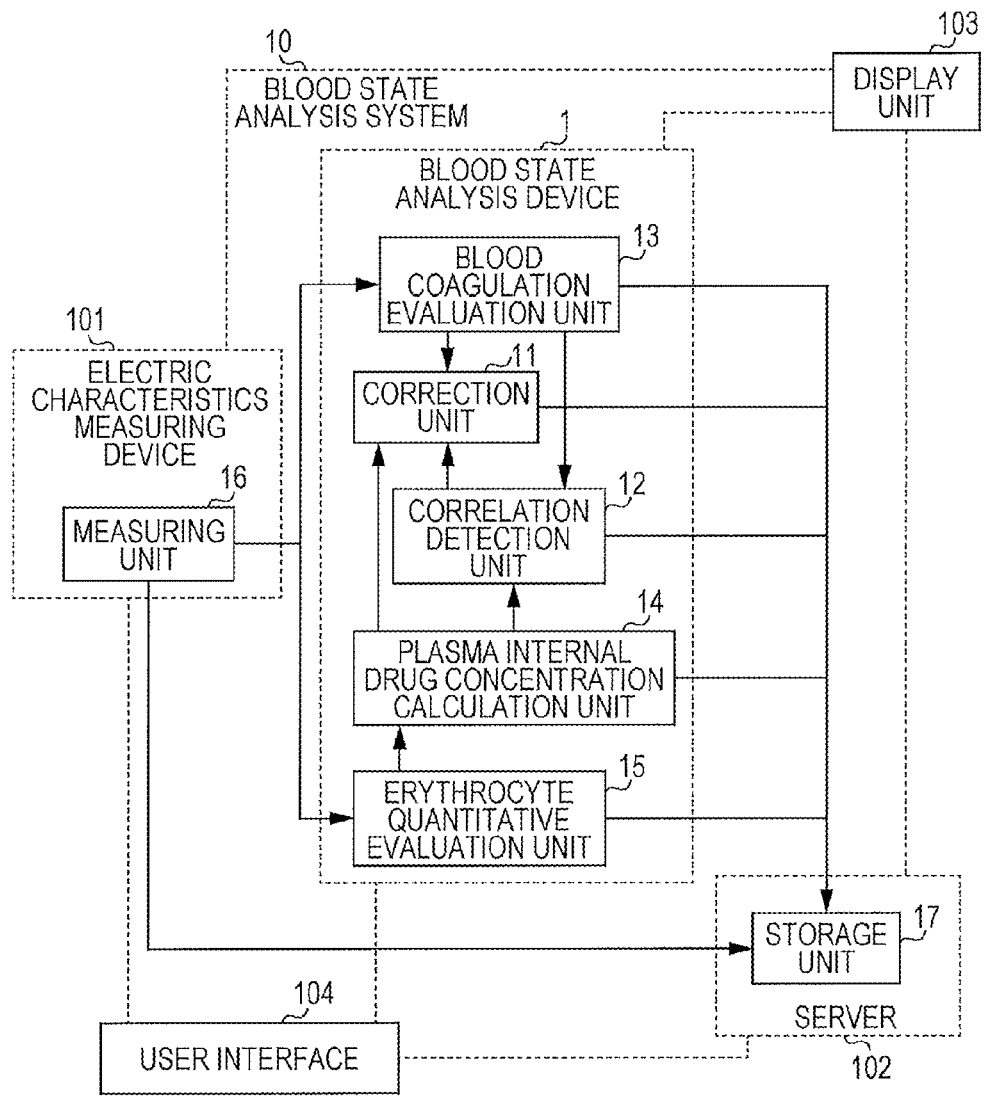

[Fig. 3]
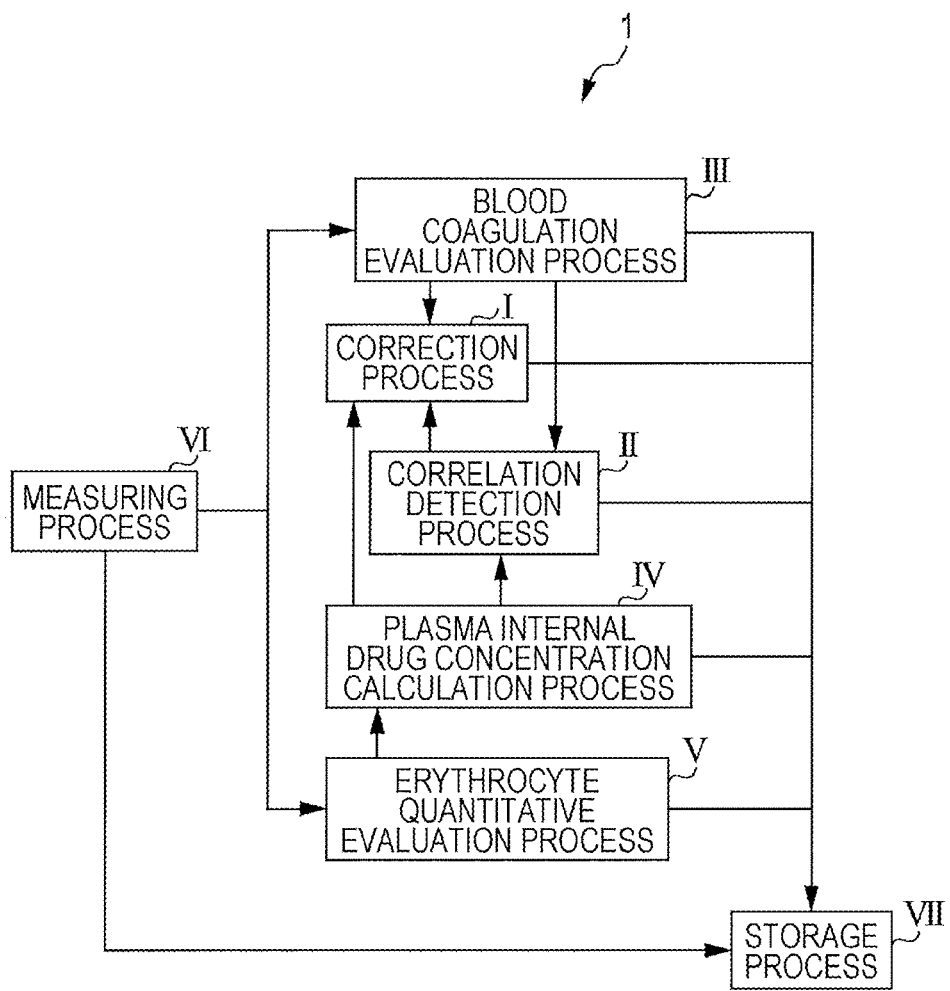

[Fig. 4]
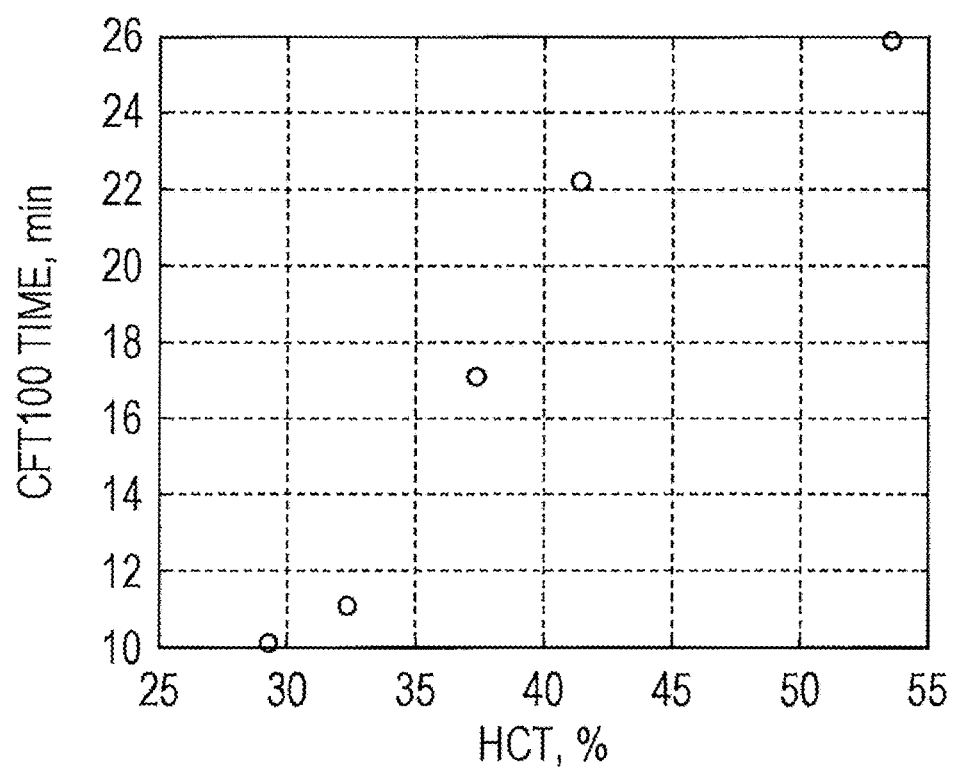

[Fig. 5-A]
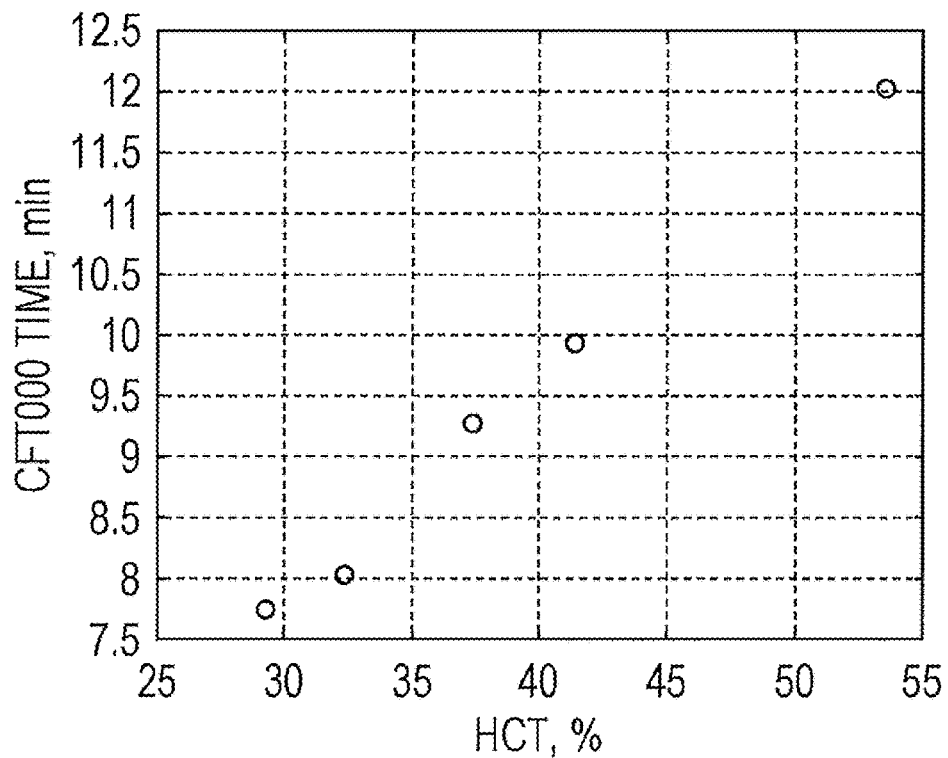
[Fig. 5-B]
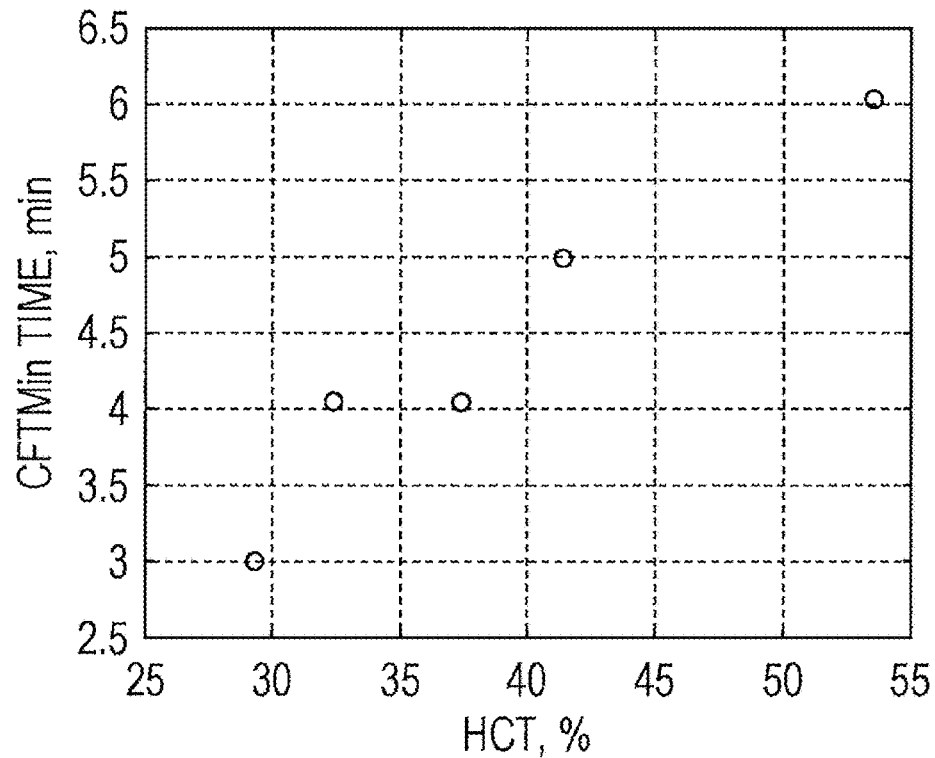

[Fig. 5-C]
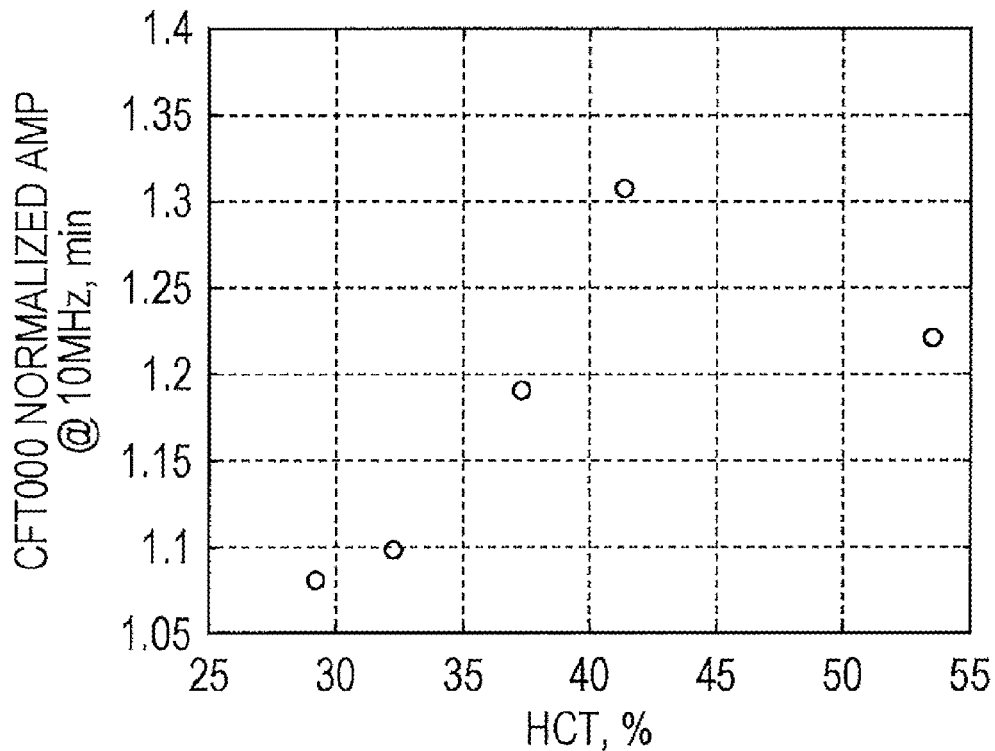
[Fig. 5-D]
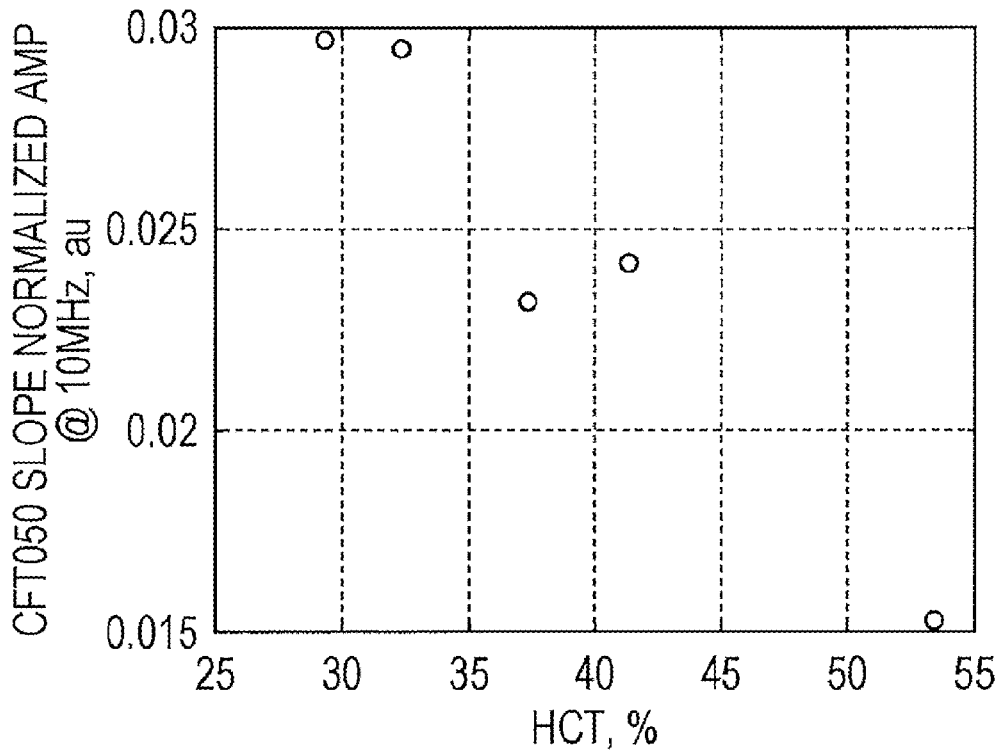

[Fig. 6]
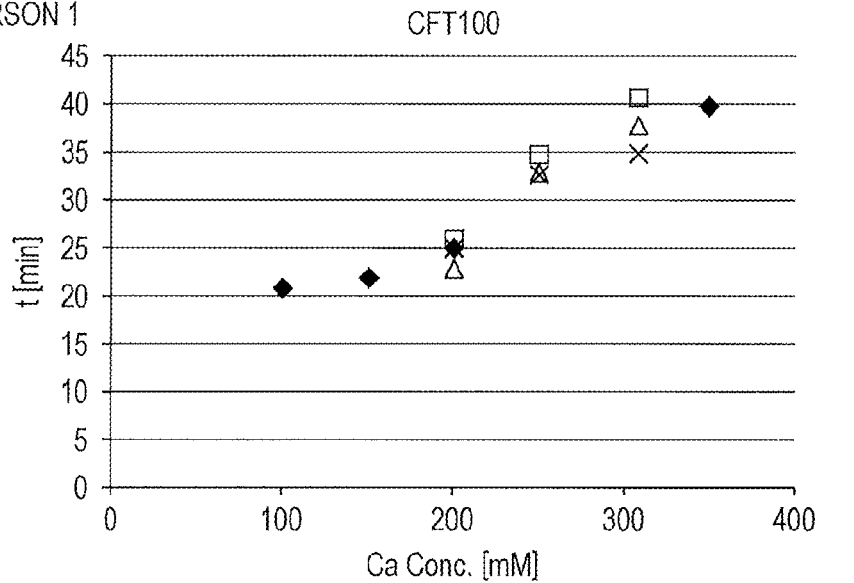
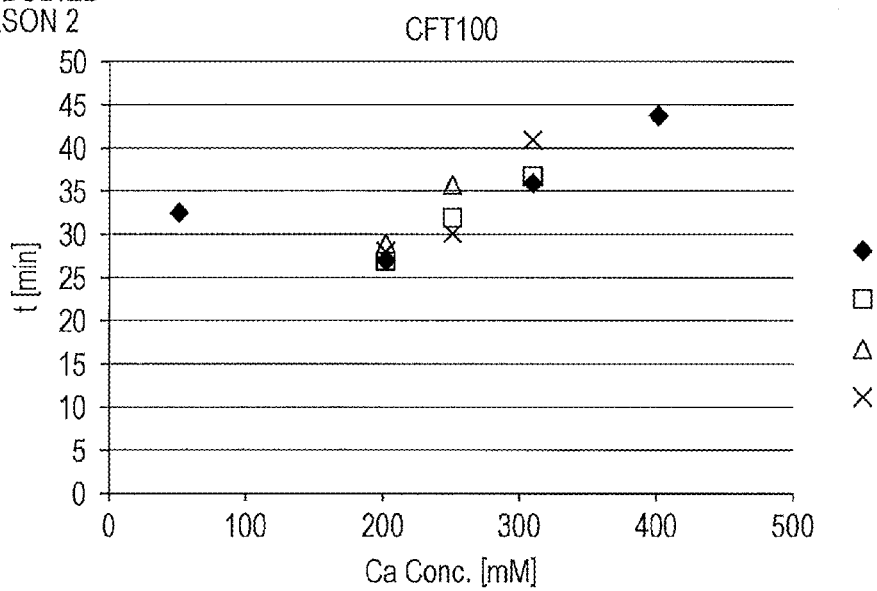

[Fig. 7]
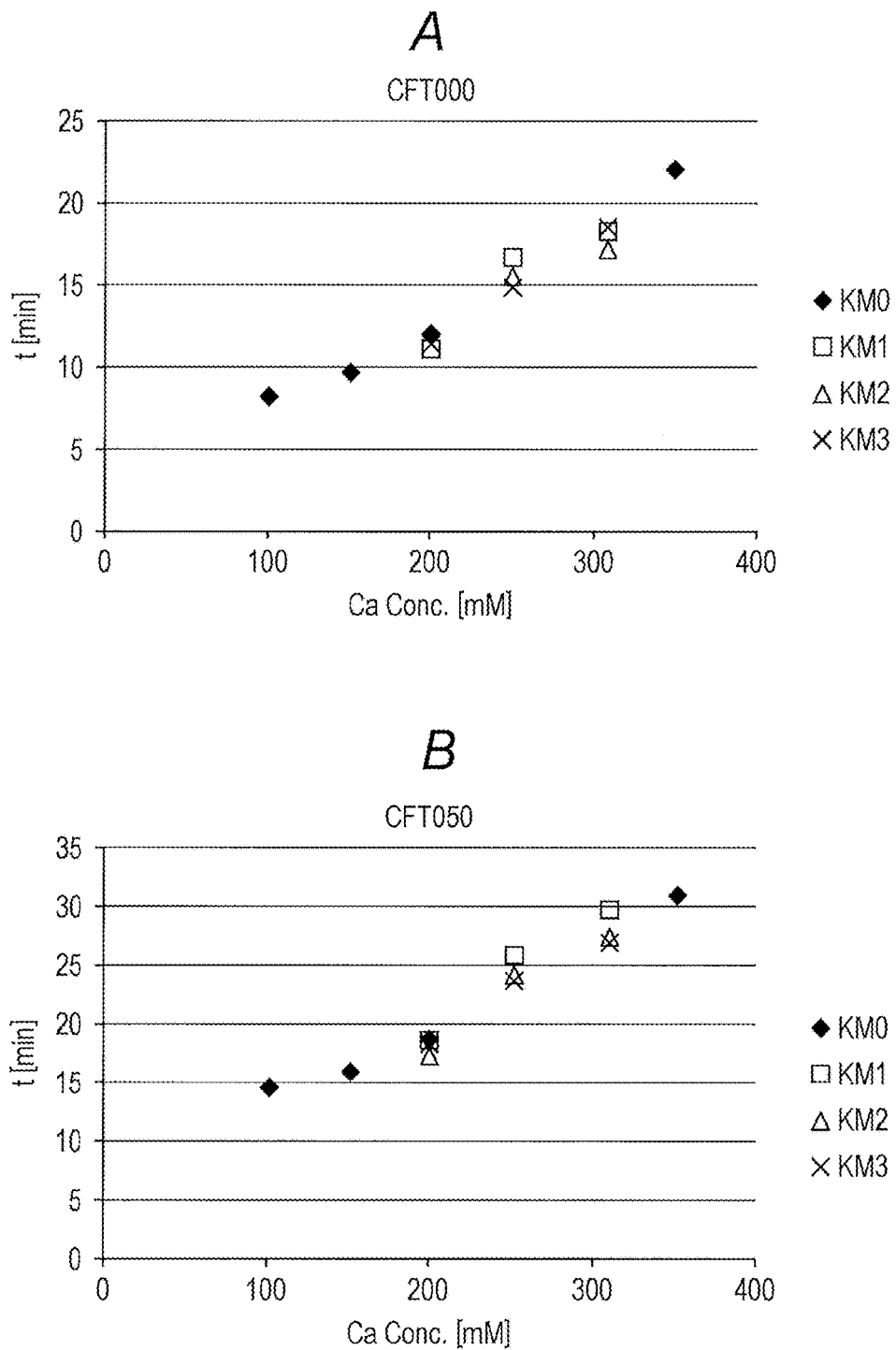

BLOOD STATE ANALYSIS DEVICE, BLOOD STATE ANALYSIS SYSTEM, BLOOD STATE ANALYSIS METHOD, AND STORAGE DEVICE

CROSS REFERENCE TO RELATED APPLICATIONS

The application claims the benefit of Japanese Priority Patent Application JP 2014-085511, filed Apr. 17, 2014, the entire contents of which are incorporated herein by reference. This application is a national stage filing under 35 U.S.C. 371 of International Patent Application Serial No. PCT/JP2015/001989, filed Apr. 9, 2015, entitled "BLOOD STATE ANALYSIS DEVICE, BLOOD STATE ANALYSIS SYSTEM, BLOOD STATE ANALYSIS METHOD, AND STORAGE DEVICE".

TECHNICAL FIELD

The present technology relates to a blood state analysis device. In particular, the present technology relates to a device that analyzes a state of a blood sample while at least one drug selected from a group including an anticoagulation treatment releasing agent, a coagulation activator, an anticoagulant, a platelet activator, and an antiplatelet drug is added to the blood sample, a blood state analysis system, a blood state analysis method, and a program causing a computer to realize the method.

BACKGROUND ART

As a method of obtaining a volume fraction of cells in a cell suspension, a technique of using low-frequency electric conductivity (frequency of 100 kHz or less) of the suspension and low-frequency electric conductivity (frequency of 100 kHz or less) of a solvent containing no cell is known (NPL 1). In a suspension in which, for example, spherical cells are thinly dispersed, the volume fraction of cells can be obtained as Formula (1) shown below:

[Math. 1]

$$\phi = 2\frac{\kappa_a - \kappa_b}{2\kappa_a + \kappa_b} \quad (1)$$

ϕ: Volume fraction
$\kappa_a$: Electric conductivity of the solvent
$\kappa_b$: Electric conductivity of the suspension If the shape of suspended cells is not spherical, on the other hand, it is also necessary to consider the shape of cells and in a suspension in which, for example, cells in a spheroidal shape are thinly dispersed, the volume fraction of cells can be obtained as Formula (2) shown below:

[Math. 2]

$$\phi = 9\left(\frac{1}{1-Lz} + \frac{2}{1-L(x=y)}\right)^{-1} \cdot \frac{\kappa_a - \kappa_b}{2\kappa_a + \kappa_b} \quad (2)$$

ϕ: Volume fraction
$\kappa_a$: Electric conductivity of the solvent
$\kappa_b$: Electric conductivity of the suspension
Lx, Ly, Lz: Parameters related to the shape or the like of the spheroid For a concentrated suspension in which the cell density is high and which is not handled as a thinly dispersed system, it is necessary to use another formula that takes an interaction between cells into consideration.

However, these conventional methods need to use electric conductivity of a solvent that does not contain cells and it is difficult to obtain the volume fraction of cells from data of a suspension only. In addition, cells need to be dispersed in the solvent without being agglutinated. Thus, in the case of, for example, blood containing plasma components, rouleaux and agglutination of erythrocytes are formed and therefore, it is difficult to determine the volume fraction of erythrocytes and so on by the conventional method. In addition, the degree of rouleaux or agglutination changes in various ways depending on the flow of blood or the time after leaving at rest and therefore, it is difficult to determine a formula that factors in the degree of rouleaux or agglutination and currently, such a formula is not known.

As the common blood coagulation test, blood coagulation tests including the prothrombin time (PT) and the activated partial thromboplastin time (APTT) are known. These are methods that analyze proteins contained in plasma obtained by centrifuging a blood sample and involved in a coagulation reaction. It has been considered that this field is technically established and needs in medical sites are almost met.

However, in order to respond to needs of wanting to appropriately and handily test comprehensive pathologic conditions of coagulation of a patient in the perioperative (acute phase) treatment in which promptness is demanded, the aforementioned methods are insufficient. More specifically, for example, in a major operation such as a heart operation involving extracorporeal circulation by an artificial heart-lung machine, treatment of major physical trauma, or a liver transplantation operation, not only surgical bleeding, but also bleeding caused by anomalous coagulation may continue. Nevertheless, cell components such as platelets and erythrocytes playing an important role in the coagulation reaction in the body are removed by centrifugation in the conventional coagulation test and thus, test results are frequently at variance with actual clinical pathologic conditions.

In addition, coagulating pathologic conditions of a patient may greatly vary throughout a perioperative period and may often change from a bleeding tendency to a thrombus tendency, but PT and APTT are tests of the bleeding tendency and a sensitive test method of the thrombus tendency is not yet been established.

As a comprehensive coagulation test for an acute period, thromboelastometry that mechanically measures viscoelasticity changes accompanying the blood coagulation process has been commercially introduced by European and American companies as TEG (registered trademark) or ROTEM (registered trademark). However, (1) measurements are not automated and measurement results depend on the procedure of the measuring person, (2) measurements are likely to be subject to vibration, (3) the quality control (QC) procedure is complex and the reagent for QC is expensive, and (4) a skilled labor is necessary for interpretation of an output signal (thromboelastogram) are considered to be main reasons that widespread use thereof is not achieved. Thus, for patients who do not need blood transfusion if a comprehensive coagulation test is performed, blood preparations are currently used empirically as a means of prevention, which increases not only risks of infectious disease, but also waste of blood preparations and medical expenses.

In recent years, technologies that handily and correctly evaluate the degree of coagulation of blood are under development. For example, Patent Literature 1 discloses a technology that acquires information about blood coagulation from the dielectric constant of blood and "A blood coagulation system analysis device including: a pair of electrodes; an applying unit that applies an alternating voltage to the pair of electrodes at predetermined intervals; a measuring unit that measures a dielectric constant of blood disposed between the pair of electrodes; and an analysis unit that analyzes a degree of working of a blood coagulation system using the dielectric constant of the blood measured at the time intervals after anticoagulant action working on the blood is released" is described.

As a blood specimen for this method, blood collected from a vein while using citric acid as an anticoagulant is generally used. An anticoagulation treatment releasing agent such as a calcium chloride solution is used immediately before the measurement is started to release the anticoagulation action and then, measurements are made after a blood coagulation reaction is in progress.

CITATION LIST

Patent Literature

PTL 1: JP 2010-181400 A

Non Patent Literature

NPL 1: Phys. Med. Biol. 54 (2009) 2395-2405

SUMMARY

Technical Problem

As described above, technologies to evaluate blood coagulation capacity make progress day by day, but on the other hand, it has become clear in recent years that separately from the clinical state of a patient, an artifact is generated by some other factor.

Therefore, it is desirable to provide a technology capable of handily and accurately evaluating the blood coagulation capacity.

Solution to Problem

According to some embodiments, a blood state analysis device that analyzes a state of a blood sample comprising a plasma and at least one reagent may comprise a correction unit configured to correct a measured blood coagulation evaluation result of the blood sample based on a relation between reference concentrations of the at least one reagent in plasma and reference blood coagulation evaluation results. In some aspects, the at least one reagent is an anticoagulation treatment releasing agent, a coagulation activator, an anticoagulant, a platelet activator, an antiplatelet drug, or a combination thereof and is present in the blood sample.

According to some implementations, a blood state analysis system comprises an electrical characteristics measuring device including a measuring unit configured to measure electrical characteristics of a blood sample comprising a plasma. The blood state analysis system may further include a blood state analysis device configured to analyze a state of the blood sample, wherein at least one reagent that is an anticoagulation treatment releasing agent, a coagulation activator, an anticoagulant, a platelet activator, an antiplatelet drug, or a combination thereof is present in the blood sample. In some implementations, the blood state analysis system further includes a correction unit configured to correct a measured blood coagulation evaluation result of the blood sample based on a relation between reference concentrations of the at least one reagent in plasma and reference blood coagulation evaluation results.

Methods are also contemplated. According to some embodiments, a blood state analysis method that analyzes a state of a blood sample comprising a plasma and at least one reagent comprises acts of correcting a measured blood coagulation evaluation result of the blood sample based on a relation between reference concentrations of the at least one reagent in plasma and reference blood coagulation evaluation results. In some aspects, the correcting comprises correcting the measured coagulation evaluation result to a corrected coagulation evaluation result that corresponds to a reference concentration of the at least one reagent in plasma that is substantially equal to a measured concentration of the at least one reagent in the plasma of the blood sample. In further aspects, the at least one reagent is an anticoagulation treatment releasing agent, a coagulation activator, an anticoagulant, a platelet activator, an antiplatelet drug, or a combination thereof.

In some embodiments, a storage device comprises a blood state analysis program that may be used to analyze a state of a blood sample having a plasma and at least one reagent. The program may comprise computer-readable instructions that adapt a computer to correct a measured blood coagulation evaluation result of the blood sample based on a relation between reference concentrations of the at least one reagent in plasma and reference blood coagulation evaluation results, wherein the at least one reagent is an anticoagulation treatment releasing agent, a coagulation activator, an anticoagulant, a platelet activator, an antiplatelet drug, or a combination thereof.

Advantageous Effects of Invention

According to an embodiment of the present technology, the blood coagulation capacity can be evaluated handily and accurately.

However, the effect described here should not be necessarily restricted and may be any effect described in this specification.

BRIEF DESCRIPTION OF DRAWINGS

FIG. 1 is a schematic conceptual diagram schematically showing the concept of a blood state analysis device 1 according to an embodiment of the present technology.

FIG. 2 is a schematic conceptual diagram schematically showing the concept of a blood state analysis system 10 according to an embodiment of the present technology.

FIG. 3 is a flow chart of a blood state analysis method according to an embodiment of the present technology.

FIG. 4 is a graph substitute for a drawing showing a correlation between a blood coagulation time (CFT100) obtained by dielectric constant measurements and a hematocrit value in Example 1.

FIG. 5 is a graph substitute for a drawing showing the correlation between various parameters showing blood coagulation capacity obtained by dielectric constant measurements and the hematocrit value in Example 1.

FIG. 6 is a graph substitute for a drawing showing the correlation between the blood coagulation time (CFT100) obtained by dielectric constant measurements and a calcium concentration in Example 2.

FIG. 7 is a graph substitute for a drawing showing the correlation between various parameters showing blood coagulation capacity obtained by dielectric constant measurements and the calcium concentration in Example 2.

DESCRIPTION OF EMBODIMENTS

Hereinafter, preferred embodiments to carry out the present technology will be described with reference to the accompanying drawings. The embodiments described below show exemplary embodiments of the present technology and the scope of the present technology will not be thereby interpreted in a narrow sense. The description of the embodiments will be provided in the order shown below:

1. Blood state analysis device 1
   (1) Correction unit 11
   (2) Correlation detection unit 12
   (3) Blood coagulation evaluation unit 13
   (4) Plasma internal drug concentration calculation unit 14
   (5) Erythrocyte quantitative evaluation unit 15
   (6) Measuring unit 16
   (7) Storage unit 17
   (8) Blood sample
2. Blood state analysis system 10
   (1) Electric characteristics measuring device 101
   (2) Blood state analysis device 1
   (3) Server 102
   (4) Display unit 103
   (5) User interface 104
3. Blood state analysis method
   (1) Correction process I
   (2) Correlation detection process II
   (3) Blood coagulation evaluation process III
   (4) Plasma internal drug concentration calculation process IV
   (5) Erythrocyte quantitative evaluation process V
   (6) Measuring process VI
   (7) Storage process VII
4. Blood state analysis program 1. Blood State Analysis Device 1

FIG. 1 is a schematic conceptual diagram schematically showing the concept of the blood state analysis device 1 (hereinafter, also called the "device 1") according to an embodiment of the present technology. The blood state analysis device 1 according to an embodiment of the present technology is a device that analyzes the state of the blood sample while at least one drug (hereinafter, called "the drug") selected from a group including an anticoagulation treatment releasing agent, a coagulation activator, an anticoagulant, a platelet activator, and an antiplatelet drug is added and includes at least a correction unit 11. In addition, a correlation detection unit 12, a blood coagulation evaluation unit 13, a plasma internal drug concentration calculation unit 14, an erythrocyte quantitative evaluation unit 15, a measuring unit 16, or a storage unit 17 may also be included when necessary.

As the drug, for example, at least one drug can be used by freely selecting from a group including anticoagulation treatment releasing agent such as calcium chloride, calcium sulfate, calcium carbonate, and calcium acetate (that is, these are calcium salts), a coagulation activator such as a tissue factor, a contact factor, ellagic acid, kaolin, cerite, thrombin, and batroxobin, an anticoagulant such as citric acid, heparin, hirudin, EDTA, a direct thrombin inhibitor, and an activated X factor inhibitor, a platelet activator such as collagen, arachidonic acid, ADP, and thrombin, and an antiplatelet drug such as acetylsalicylic acid (aspirin), prostaglandin, a thromboxane ligase inhibitor, a thienopyridine derivative (such as ticlopidine hydrochloride, clopidogrel, and prasugrel), a PDE-3 inhibitor, a 5-serotonin receptor-2 antagonist, and a GPIIb/IIIa inhibitor.

Hereinafter, each unit will be described in detail.

(1) Correction Unit 11

The correction unit 11 corrects a blood coagulation evaluation result of the blood sample based on a correlation between the concentration of the drug in platelets and the blood coagulation evaluation result so as to correspond to the concentration of the drug present in plasma of the blood sample.

In the present technology, as will be shown in examples described later, even if the same blood specimen is used, the inventors found that parameters showing the blood coagulation capacity change depending on the concentration of the added drug in platelets. That is, the inventors found that an error arises in the blood coagulation evaluation result in accordance with the amount of the drug to be added or the ratio of plasma in the blood specimen. Thus, by correcting the blood coagulation evaluation result so as to correspond to the concentration of the drug present in the plasma, a more accurate evaluation can be made by excluding an artifact generated by changes of the concentration of the drug in the plasma.

The correction unit 11 corrects test values in the reference drug concentration based on the dependence on the concentration of test values obtained from a correlation between the concentration of the drug in the plasma and blood coagulation evaluation results or a correction function using correction constants determined by the correlation.

The correlation used for corrections by the correction unit 11 may be a preset correlation or the correlation may be determined during analysis by including the correlation detection unit 12 described later in the device 1 to be able to make corrections by the correction unit 11.

(2) Correlation Detection Unit 12

The correlation detection unit 12 determines a correlation between the concentration of the drug in the plasma and a blood coagulation evaluation result. In the blood state analysis device 1 according to an embodiment of the present technology, the correlation detection unit 12 is not prerequisite and, as described above, a preset correlation may be used, but by including the correlation detection unit 12, the correlation can be detected and corrections can be made in one device. The method of determining a blood correlation is not specifically limited and a general statistical technique may be used to determine the blood correlation and, for example, the following methods can be cited:

(a) Method of Determining Correlation Coefficients

The correlation detection unit 12 can determine the correlation by adopting a method of determining correlation coefficients from, for example, the dependence on the concentration of test values in two different plasma internal drug concentrations or more. Then, correct evaluation results can be obtained by correcting test values in the reference drug concentration by the correction unit 11 based on the obtained correlation coefficients.

The correlation coefficient is determined for each specimen in this method and therefore, a correction appropriate for each specimen can be made.

(b) Method of Determining a Correction Constant

The correlation detection unit 12 can determine the correlation by adopting a method of determining a correction constant that can be used for almost all specimens by, for example, determining a regression equation showing the dependence on the concentration of test values in two different plasma internal drug concentrations or more for each of a plurality of specimens and finding, among mathematical combinations of a coefficient or a plurality of coefficients of each regression equation, a combination having an almost constant value regardless of the specimen.

In this method, once the correction constant is determined, a correction can advantageously be made after measurement in one plasma internal drug concentration per specimen.

(3) Blood Coagulation Evaluation Unit 13

The blood coagulation evaluation unit 13 obtains the blood coagulation evaluation result by evaluating the degree of blood coagulation based on electric characteristics of a blood sample. The blood coagulation evaluation unit 13 is not prerequisite for the blood state analysis device 1 according to an embodiment of the present technology and the blood coagulation evaluation result can be obtained by, for example, another device or method in advance.

As electric characteristics of a blood sample, raw data measured by an external electric characteristics measuring device or, if the blood state analysis device 1 according to an embodiment of the present technology includes the measuring unit 16, measured by the measuring unit 16 can be used as it is. Alternatively, data obtained by eliminating noise from raw data can be used.

Electric characteristics of blood that can be used by the blood coagulation evaluation unit 13 include, for example, the dielectric constant, impedance, admittance, capacitance, conductance, conductivity, and phase angle. These electric characteristics can mutually be converted based on formulas shown in Table 1 below. Thus, for example, an evaluation result that evaluates the degree of blood coagulation using a result of dielectric constant measurement of a blood sample is the same as an evaluation result using a result of impedance measurement of the same blood sample. Most of these quantities of electricity or physical property values can be described using complex values, thereby simplifying conversion formulas.

TABLE 1

<Main quantities of electricity and physical property values that are mutually convertible>

| Quantities of electricity and physical property values | Symbol | Complex representation |
|---|---|---|
| Voltage | V | $V^* = \|V\|\exp j(\omega t + \phi)$ |
| Current | I | $I^* = \|I\|\exp j(\omega t + \varphi)$ |
| Impedance | Z | $Z^* = R + jX$ (R: Resistance, X: Reactance) |
| Admittance | Y | $Y^* = G + jB$ (G: Conductance, B: Susceptance) |
| Capacitance | C | $C^* = C - jG/\omega$ |
| Conductance | G | $G^* = G + j\omega C$ |
| Loss tangent (dielectric tangent) | D or tan$\delta$ | |
| Loss angle | $\delta$ | |
| Phase angle | $\theta$ | |
| Q value | Q | |
| Dielectric constant | $\varepsilon$ | $\varepsilon^* = \varepsilon - j\kappa/\omega\varepsilon_0$ |
| Conductivity | $\kappa$ | $\kappa^* = \kappa + j\omega\varepsilon_0\varepsilon$ |

<Formulas associating each quantity of electricity and each physical property value>

$Z^* = V^*/I^*$
$\theta = \phi - \varphi$
$Y^* = 1/Z^*$
$C = B/\omega$
$D = \tan\delta = G/\omega C = 1/Q$ TABLE 1-continued <Main quantities of electricity and physical property values that are mutually convertible>

$\varepsilon^* = C^*/C_0$
$\kappa^* = j\omega\varepsilon_0\varepsilon^*$ $\omega$: Angular frequency
$\varepsilon_0$: Dielectric constant (constant) of the vacuum
$C_0$: Constant depending on the measuring device or the like
*attached value: Complex number While electric characteristics of any frequency may be used as electric characteristics used for evaluation by the blood coagulation evaluation unit 13, it is desirable to evaluate the degree of blood coagulation from electric characteristics of a blood sample particularly at frequencies 1 kHz to 50 MHz and it is more desirable to evaluate the degree of blood coagulation from electric characteristics of a blood sample at frequencies 3 MHz to 15 MHz. This is because changes in electric characteristics due to blood coagulation are observed at frequencies 1 kHz to 50 MHz and changes in electric characteristics are observed more conspicuously at frequencies 3 MHz to 15 MHz.

(4) Plasma Internal Drug Concentration Calculation Unit 14

The plasma internal drug concentration calculation unit 14 calculates the concentration of the drug present in plasma in the blood sample. The plasma internal drug concentration calculation unit 14 is not prerequisite for the blood state analysis device 1 according to an embodiment of the present technology and the concentration of the drug present in the plasma in the blood sample can also be measured by, for example, another device or method in advance.

In the plasma internal drug concentration calculation unit 14, the plasma internal drug concentration is calculated based on the hematocrit value and/or the quantity of hemoglobin of the blood sample. A blood sample of a large hematocrit value and/or a large quantity of hemoglobin has a relatively small quantity of plasma and conversely, a blood sample of a small hematocrit value and/or a small quantity of hemoglobin has a relatively large quantity of plasma. That is, the quantity of plasma shows a negative correlation with the hematocrit value and/or the quantity of hemoglobin of the blood sample.

When the same quantity of the drug is added, a blood sample of a large hematocrit value and/or a large quantity of hemoglobin has a relatively small quantity of plasma and thus has a higher drug concentration in the plasma and conversely, a blood sample of a small hematocrit value and/or a small quantity of hemoglobin has a relatively large quantity of plasma and thus has a lower drug concentration in the plasma. That is, when the same quantity of the drug is added, the concentration of the drug present in the plasma shows a positive correlation with the hematocrit value and/or the quantity of hemoglobin of the blood sample. Using this correlation, the plasma internal drug concentration calculation unit 14 calculates the plasma internal drug concentration based on the hematocrit value and/or the quantity of hemoglobin of the blood sample.

Measured values determined by another device or method in advance may also be used as the hematocrit value and/or the quantity of hemoglobin of the blood sample or the hematocrit value and/or the quantity of hemoglobin obtained by the erythrocyte quantitative evaluation unit 15 described later after the erythrocyte quantitative evaluation unit 15 being included in the device 1 may also be used.

(5) Erythrocyte Quantitative Evaluation Unit 15

The erythrocyte quantitative evaluation unit 15 evaluates the hematocrit value and/or the quantity of hemoglobin based on electric characteristics of the blood sample. The erythrocyte quantitative evaluation unit 15 is not prerequisite for the blood state analysis device 1 according to an embodiment of the present technology and the hematocrit value and/or the quantity of hemoglobin of the blood sample can be measured by, for example, another device or method in advance.

Electric characteristics of blood that can be used by the erythrocyte quantitative evaluation unit 15 are the same as those that can be used by the blood coagulation evaluation unit 13 and thus, the description thereof here is omitted.

While electric characteristics of any frequency may be used as electric characteristics used for evaluation by the erythrocyte quantitative evaluation unit 15, it is desirable to evaluate the hematocrit value and/or the quantity of hemoglobin from electric characteristics of the blood sample, particularly in the present technology, at frequencies 2 to 25 MHz and it is more desirable to evaluate the hematocrit value and/or the quantity of hemoglobin from electric characteristics of the blood sample at frequencies 2 to 10 MHz. This is because electric characteristics of the blood sample at frequencies 2 to 25 MHz are less likely to be subject to erythrocyte rouleaux, variations are small until the blood coagulation reaction reaches a certain level, and correlate with the hematocrit value and the quantity of hemoglobin obtained from a general conventional blood test. In addition, an electric response of blood at frequencies higher than 10 MHz becomes weaker and the influence of noise becomes relatively stronger and therefore, a more correct evaluation can be made by using electric characteristics of 10 MHz or less.

Electric characteristics of blood used by the erythrocyte quantitative evaluation unit 15 are desirably used in an earlier stage after starting measurements if possible. More specifically, it is desirable to use electric characteristics within three minutes after anticoagulation being released by an anticoagulant. This is because the influence of rouleaux and coagulation of blood can be minimized within three minutes after anticoagulation being released. When measurements are made by adding a coagulation activator, the time before blood coagulation starts is short and therefore, it is desirable to use electric characteristics within one minute after anticoagulation is released.

In addition to the correction unit 11, the blood state analysis device 1 according to an embodiment of the present technology can include the blood coagulation evaluation unit 13, the plasma internal drug concentration calculation unit 14, and the erythrocyte quantitative evaluation unit 15. By including these units, a series of processes of evaluating the blood coagulation capacity and the hematocrit value and/or the quantity of hemoglobin from electric characteristics obtained by one measurement, calculating the concentration of drug in the plasma from the obtained hematocrit value and/or quantity of hemoglobin, and correcting the obtained blood coagulation capacity evaluation result in accordance with the calculated concentration of drug in the plasma can be performed in one device. As a result, the reduction of analysis costs and shortening of the analysis time can be realized.

When both of the blood coagulation evaluation unit 13 and the erythrocyte quantitative evaluation unit 15 are included in the blood state analysis device 1 according to an embodiment of the present technology, electric characteristics used for evaluation by both evaluation units may be electric characteristics at the same frequency, but the blood coagulation evaluation unit 13 may evaluate the degree of blood coagulation based on electric characteristics at the first frequency of a blood sample and the erythrocyte quantitative evaluation unit 15 may determine the hematocrit value and/or the quantity of hemoglobin based on electric characteristics at the second frequency, which is different from the first frequency, of the blood sample. For example, as described above, desirable frequencies of electric characteristics used for evaluation are different from the blood coagulation evaluation unit 13 and the erythrocyte quantitative evaluation unit 15 and therefore, more correct evaluations can be made by using electric characteristics in the frequency band more appropriate for each.

(6) Measuring Unit 16

The measuring unit 16 measures electric characteristics of a blood sample. The measuring unit 16 is not prerequisite for the blood state analysis device 1 according to an embodiment of the present technology and data measured by an external electric characteristics measuring device may also be used.

The measuring unit 16 may include one or a plurality of blood sample holders. The blood sample holder is not prerequisite for the blood state analysis device 1 and, for example, the measuring unit 16 may be designed in a form in which a publicly known cartridge type container for measurement can be installed.

When the blood sample holder is included in the measuring unit 16, the form of the blood sample holder is not particularly limited as long as a blood sample to be measured can be held inside the measuring unit 16 and can be designed freely. For example, one or a plurality of cells provided on a substrate can be made to function as blood sample holders or one or a plurality of containers can be made to function as blood sample holders.

When one or a plurality of containers is made to function as blood sample holders, the form thereof is not particularly limited and can freely be designed in accordance with the state of a blood sample or the measuring method such as a cylinder, a polygonal cylinder whose cross section is polygonal (triangular, quadrangular or more), a cone, a polygonal cone whose cross section is polygonal (triangular, quadrangular or more), or a form combining one or two or more of these forms as long as a blood sample to be measured can be held.

Also, the material constituting the container is not particularly limited and can freely be selected within the range in which the state of a blood sample to be measured or the purpose of measurement is not affected. In the present technology, it is desirable to form the container by using a resin particularly from the viewpoint of ease of processing and molding. Also, the type of resin that can be used in the present technology is not particularly limited and one type or two or more types of resin that can be applied to holding a blood sample can freely be selected and used. For example, a hydrophobic and insulating polymer, copolymer, or blend polymer of polypropylene, polymethyl methacrylate, polystyrene, acrylic, polysulfone, and polytetrafluoroethylene can be cited. In the present technology, among these resins, it is desirable to form a blood sample holder from at least one resin selected particularly from polypropylene, polystyrene, acrylic, and polysulfone. This is because these resins have a property of low coagulation activity for blood.

The blood sample holder is desirably configured to be sealable while a blood sample is held. However, the blood sample holder may not be airtightly configured if the time necessary for measuring electric characteristics of a blood sample can be stagnated and measurements are not affected.

The concrete method of introducing and sealing a blood sample in the blood sample holder is not particularly limited and the blood sample can be introduced in a free manner in accordance with the form of the blood sample holder. For example, the method of providing a cap portion in the blood sample holder and closing the cap portion for sealing after a blood sample being introduced using a pipette or the like and the method of piercing the blood sample holder with an injection needle from the outer surface and after a blood sample is injected, filling a pierced portion of the injection needle with grease or the like for sealing can be considered.

The measuring unit 16 can include one or a plurality of applying units. The applying unit is not prerequisite for the blood state analysis device 1 and, for example, an external applying device can be used by designing the blood sample holder such that an electrode can be inserted from outside.

The applying unit applies a predetermined voltage to a blood sample at set measuring intervals by starting when an instruction to start measurement is received or the blood state analysis device 1 is turned on.

The number of electrodes used as a portion of the applying unit and the material forming the electrode are not particularly limited as long as the effects of the present technology are not marred and can be configured by using a freely selected number of electrodes and a freely selected material. For example, titanium, aluminum, stainless, platinum, gold, copper, and graphite can be cited. In the present technology, among these materials, it is desirable to form an electrode from an electric conductive material containing particularly titanium. This is because titanium has a property of low coagulation activity for blood.

The measuring unit 16 can also make a plurality of measurements. Methods of making a plurality of measurements include, for example, a method of making a plurality of measurements simultaneously by including a plurality of the measuring units 16, a method of making a plurality of measurements by causing the one measuring unit 16 to scan, a method of making a plurality of measurements by moving the blood sample holder, and a method of including a plurality of the measuring units 16 and selecting one or the plurality of measuring units 16 that actually make measurements by switching.

(7) Storage Unit 17

The blood state analysis device 1 according to an embodiment of the present technology can include the storage unit 17 that stores correction results of corrections made by the correction unit 11, correlations determined by the correlation detection unit 12, each evaluation result of evaluation made by the blood coagulation evaluation unit 13 and/or the erythrocyte quantitative evaluation unit 15, plasma internal drug concentrations calculated by the plasma internal drug concentration calculation unit 14, and measurement results of measurements made by the measuring unit 16. The storage unit 17 is not prerequisite for the blood state analysis device 1 according to an embodiment of the present technology and each result may be stored by connecting an external storage device.

In the blood state analysis device 1 according to an embodiment of the present technology, the storage unit 17 may be provided separately for each unit or the one storage unit 17 may be designed to store various results obtained by each unit.

(8) Blood Sample

In the blood state analysis device 1 according to an embodiment of the present technology, blood samples that can be measured are not particularly limited as long as the sample contains blood and can be freely selected. As concrete examples of the blood sample, whole blood or a diluent thereof and a blood sample to which a drug other than the above drug is added can be cited.

2. Blood State Analysis System 10

FIG. 2 is a schematic conceptual diagram schematically showing the concept of the blood state analysis system 10 according to an embodiment of the present technology. The blood state analysis system 10 according to an embodiment of the present technology roughly includes at least electric characteristics measuring device 101 and the blood state analysis device 1. If necessary, the blood state analysis system 10 may also include a server 102, a display unit 103, or a user interface 104. Hereinafter, each unit will be described in detail.

(1) Electric Characteristics Measuring Device 101

The electric characteristics measuring device 101 includes the measuring unit 16 that measures electric characteristics of a blood sample. Details of the measuring unit 16 are the same as those of the measuring unit 16 in the aforementioned blood state analysis device 1.

(2) Blood State Analysis Device 1

The blood state analysis device 1 is a device that analyzes the state of the blood sample while the drug is added and includes at least the correction unit 11. If necessary, the correlation detection unit 12, the blood coagulation evaluation unit 13, the plasma internal drug concentration calculation unit 14, or the erythrocyte quantitative evaluation unit 15 may also be included. Details of each unit included in the blood state analysis device 1 are the same as those of the aforementioned blood state analysis device 1.

(3) Server 102

The server 102 includes the storage unit 17 that stores measurement results by the electric characteristics measuring device 101 and/or analysis results by the blood state analysis device 1. Details of the storage unit 17 are the same as those of the storage unit 17 in the aforementioned blood state analysis device 1.

(4) Display Unit 103

The display unit 103 displays correction results of corrections made by the correction unit 11, correlations determined by the correlation detection unit 12, each evaluation result of evaluation made by the blood coagulation evaluation unit 13 and/or the erythrocyte quantitative evaluation unit 15, plasma internal drug concentrations calculated by the plasma internal drug concentration calculation unit 14, and measurement results of measurements made by the measuring unit 16. A plurality of the display units 103 may be provided for each type of data or results, but the one display unit 103 may display all data or results.

(5) User Interface 104

The user interface 104 is a region operated by the user. The user can access each unit of the blood state analysis system 10 according to an embodiment of the present technology through the user interface 104.

In the blood state analysis system 10 according to an embodiment of the present technology described above, the electric characteristics measuring device 101, the blood state analysis device 1, the server 102, the display unit 103, and the user interface 104 may each be connected via a network.

3. Blood State Analysis Method

FIG. 3 is a flow chart of a blood state analysis method according to an embodiment of the present technology. The blood state analysis method according to an embodiment of the present technology is a method of analyzing the state of the blood sample while the drug is added and performs at least a correction process I. If necessary, a correlation detection process II, a blood coagulation evaluation process III, a plasma internal drug concentration calculation process IV, an erythrocyte quantitative evaluation process V, a measuring process VI, or a storage process VII may also be performed. Hereinafter, each process will be described in detail.

(1) Correction Process I

In the correction process I, a blood coagulation evaluation result of the blood sample is corrected based on a correlation between the concentration of the drug in the plasma and the blood coagulation evaluation result so as to correspond to the concentration of the drug present in the plasma in the blood sample. Details of the correction method executed in the correction process I are the same as those of the correction method executed by the correction unit 11 of the aforementioned blood state analysis device 1.

(2) Correlation Detection Process II

In the correlation detection process II, a correlation between the concentration of the drug in the plasma and a blood coagulation evaluation result is determined. The correlation detection process II is not prerequisite for the blood state analysis method according to an embodiment of the present technology and, as described above, a preset correlation may also be used. Details of the detection method executed in the correlation detection process II are the same as those of the detection method executed by the correlation detection unit 12 of the aforementioned blood state analysis device 1.

(3) Blood Coagulation Evaluation Process III blood coagulation evaluation process III, the blood coagulation evaluation result is obtained by evaluating the degree of blood coagulation based on electric characteristics of the blood sample. The blood coagulation evaluation process III is not prerequisite for the blood state analysis method according to an embodiment of the present technology and the blood coagulation evaluation result may also be obtained by, for example, another device or method in advance. Details of the evaluation method executed in the blood coagulation evaluation process III are the same as those of the evaluation method executed by the blood coagulation evaluation unit 13 of the aforementioned blood state analysis device 1.

(4) Plasma Internal Drug Concentration Calculation Process IV

In the plasma internal drug concentration calculation process IV, the concentration of the drug present in the plasma in the blood sample is calculated. The plasma internal drug concentration calculation process IV is not prerequisite for the blood state analysis method according to an embodiment of the present technology and the concentration of the drug present in the plasma in the blood sample may be calculated by another device or method in advance. Details of the calculation method executed in the plasma internal drug concentration calculation process IV are the same as those of the calculation method executed by the plasma internal drug concentration calculation unit 14 of the aforementioned blood state analysis device 1.

(5) Erythrocyte Quantitative Evaluation Process V

In the erythrocyte quantitative evaluation process V, the hematocrit value and/or the quantity of hemoglobin is evaluated based on electric characteristics of the blood sample. The erythrocyte quantitative evaluation process V is not prerequisite for the blood state analysis method according to an embodiment of the present technology and the hematocrit value and/or the quantity of hemoglobin of the blood sample may also be measured by, for example, another device or method in advance. Details of the evaluation method executed in the erythrocyte quantitative evaluation process V are the same as those of the evaluation method executed by the erythrocyte quantitative evaluation unit 15 of the aforementioned blood state analysis device 1.

(6) Measuring Process VI

In the measuring process VI, electric characteristics of the blood sample are measured. The measuring process VI is not prerequisite for the blood state analysis method according to an embodiment of the present technology and data measured by another electric characteristics measuring method may also be used. Details of the measuring method executed in the measuring process VI are the same as those of the measuring method executed by the measuring unit 16 of the aforementioned blood state analysis device 1.

(7) Storage Process VII

In the storage process VII, correction results of corrections made in the correction process I, correlations determined in the correlation detection process II, each evaluation result of evaluation made in the blood coagulation evaluation process III and/or the erythrocyte quantitative evaluation process V, plasma internal drug concentrations calculated in the plasma internal drug concentration calculation process IV, and measurement results of measurements made in the measuring process VI are stored. The storage process VII is not prerequisite for the blood state analysis method according to an embodiment of the present technology and an analysis may be conducted each time without storing each result.

4. Blood State Analysis Program

The blood state analysis program according to an embodiment of the present technology is a program used for analysis of the state of the blood sample while the drug is added, wherein a computer is caused to realize a correction function that corrects a blood coagulation evaluation result of the blood sample based on a correlation between the concentration of the drug in the plasma and the blood coagulation evaluation result so as to correspond to the concentration of the drug present in the plasma in the blood sample. If necessary, the computer can also be caused to realize a correlation detection function, a blood coagulation evaluation function, a plasma internal drug concentration calculation function, an erythrocyte quantitative evaluation function, a measuring function, or a storage function.

In other words, the blood state analysis program according to an embodiment of the present technology is a program that causes a computer to realize the aforementioned blood state analysis method according to an embodiment of the present technology. Therefore, details of each function are the same as those of each process of the aforementioned blood state analysis method and the description thereof is omitted here.

Example 1

Hereinafter, the present technology will be described in more detail based on examples. The examples described below show exemplary examples of the present technology and the scope of the present technology will not be thereby interpreted in a narrow sense.

In Example 1, correlations between parameters of the blood coagulation capacity obtained from electric characteristics of the blood sample and the hematocrit value are examined. In the present example, the dielectric constant is used as an example of electric characteristics of the blood sample.

<Experimental Method>

(1) Preparation of the Hematocrit Value of the Blood Sample

Venous blood of an able-bodied person is collected by using a vacuum blood collecting tube (quantity of collected blood: 1.8 mL, six tubes) including citric acid. The first tube is discarded without being used and for the remaining five tubes, erythrocytes are precipitated to a lower portion of the blood collecting tube by centrifugation (300 g'10 min) under mild conditions and a portion of supernatant fluid of one blood collecting tube is taken and added to another. Next, erythrocytes are uniformly dispersed by re-stirring in each blood collecting tube. In this manner, blood samples of different hematocrit values are prepared.

(2) Measurement of Electric Characteristics

Each blood sample prepared as described above is kept at 37° C. and a small quantity of a calcium chloride solution is added immediately before the start of measurement to start a blood coagulation reaction. The dielectric constant of each blood sample is measured at temperature 37° C. in the frequency band of 10 MHz.

<Result>

FIG. 4 shows a correlation between the blood coagulation time (CFT100) obtained by the dielectric constant measurement and the hematocrit value. It is evident that, as shown in FIG. 4, the blood coagulation time increases with an increasing hematocrit value.

FIG. 5 shows correlations between other parameters obtained by the dielectric constant measurement and the hematocrit value. In FIG. 5, A shows a correlation between the coagulation start time and the hematocrit value, B shows a correlation between the time when the minimum dielectric constant increase intensity is produced and the hematocrit value, C shows a correlation between the dielectric constant increase intensity during blood coagulation and the hematocrit value, and D shows a correlation between the rate of coagulation and the hematocrit value.

As shown in FIG. 5, the coagulation start time (see A), the time when the minimum dielectric constant increase intensity is produced (see B), and the dielectric constant increase intensity during blood coagulation (see C) generally increases with an increasing hematocrit value and the rate of conjugation (see D) generally decreases with an increasing hematocrit value.

Example 2

In Example 2, correlations between parameters of the blood coagulation capacity obtained from electric characteristics of the blood sample and the concentration in the plasma of a drug to be added are examined. In the present example, the dielectric constant is used as an example of electric characteristics of the blood sample.

<Experimental Method>

(1) Measurement of Electric Characteristics

Venous blood of two able-bodied persons is collected by using a vacuum blood collecting tube (quantity of collected blood: 1.8 mL, six tubes) including citric acid. The first tube is discarded without being used and the remaining five tubes are kept at 37° C. in advance and 12 mL of a calcium chloride solution per 180 mL of blood is added immediately before the start of measurement by changing the concentration thereof in the range from 100 mM to 400 mM to start a blood coagulation reaction. The dielectric constant of each blood sample is measured at temperature 37° C. in the frequency band of 10 MHz.

<Result>

FIG. 6 shows a correlation between the blood coagulation time (CFT100) obtained by the dielectric constant measurement and the hematocrit value. It is evident that, as shown in FIG. 6, the blood coagulation time increases with an increasing calcium concentration.

FIG. 7 shows correlations between other parameters obtained by the dielectric constant measurement and the calcium concentration. In FIG. 7, A shows a correlation between the coagulation start time and the calcium concentration and B shows a correlation between the CFT50 time (middle point between the time when the minimum dielectric constant increase intensity is produced and the dielectric coagulation time) and the calcium concentration.

As shown in FIG. 7, it is evident that both parameters increase with an increasing calcium concentration.

Example 2 shows a result of changing the concentration of calcium chloride added to the blood sample whose hematocrit value is constant. That is, it is evident that parameters indicating the blood coagulation capacity change depending on the calcium concentration in the plasma.

Results of Example 1 and Example 2 show that if the calcium concentration in blood (plasma) is unknown, reliability of the blood coagulation time as a test result decreases. If, for example, a blood coagulation time longer than the normal value is obtained as a test result, it turns out that it is difficult to immediately determine whether the test result shows a bleeding tendency due to a degraded blood coagulation capacity or the test result is caused simply by a higher calcium concentration in the plasma. This is because even if the same quantity of an aqueous calcium solution of the same concentration is added, the effective concentration of calcium present in the plasma changes if the hematocrit value of the blood sample is different.

From the above result, it turns out that a blood coagulation evaluation result changes depending on the concentration of the drug present in the plasma and therefore, a more accurate evaluation can be made by correcting the blood coagulation evaluation result so as to correspond to the concentration of the drug present in the plasma.

It also turns out that the concentration of the drug present in the plasma in the blood sample can be calculated based on the hematocrit value and/or the quantity of hemoglobin of the blood sample.

The present technology can also adopt the configuration shown below:

(1)

A blood state analysis device that analyzes a state of a blood sample comprising a plasma and at least one reagent, the device comprising:

a correction unit configured to correct a measured blood coagulation evaluation result of the blood sample based on a relation between reference concentrations of the at least one reagent in plasma and reference blood coagulation evaluation results, wherein the at least one reagent is an anticoagulation treatment releasing agent, a coagulation activator, an anticoagulant, a platelet activator, an antiplatelet drug, or a combination thereof and is present in the blood sample.

(2)

The blood state analysis device according to (1), wherein the correction unit is further configured to correct the measured coagulation evaluation result to a corrected coagulation evaluation result that corresponds to a reference concentration of the at least one reagent in plasma that is substantially equal to a measured concentration of the at least one reagent in the plasma of the blood sample.

(3)

The blood state analysis device according to (1) or (2), wherein the correlation is predetermined.

(4)

The blood state analysis device according to (1) or (2), further comprising: a correlation detection unit configured to determine the relation between the reference concentrations of the at least one reagent in the plasma and the reference blood coagulation evaluation results.

(5)

The blood state analysis device according to any of (1) to (4), further comprising: a blood coagulation evaluation unit configured to obtain the blood coagulation evaluation result by evaluating a degree of blood coagulation based on electrical characteristics of the blood sample.

(6)

The blood state analysis device according to any of (1) to (5), further comprising: a plasma internal reagent concentration calculation unit configured to calculate a concentration of the at least one reagent present in the plasma in the blood sample based on a hematocrit value and/or a quantity of hemoglobin of the blood sample.

(7)

The blood state analysis device according to any of (1) to (6), further comprising: an erythrocyte quantitative evaluation unit configured to determine a hematocrit value and/or a quantity of hemoglobin of the blood sample based on electrical characteristics of the blood sample.

(8)

The blood state analysis device according to (7), further comprising: a plasma internal reagent concentration calculation unit configured to calculate a concentration of the at least one reagent present in the plasma in the blood sample based on the hematocrit value and/or the quantity of hemoglobin obtained by the erythrocyte quantitative evaluation unit.

(9)

The blood state analysis device according to any of (1) to (8), further comprising: a measuring unit configured to measure electrical characteristics of the blood sample.

(10)

The blood state analysis device according to (9), further comprising:

a blood coagulation evaluation unit configured to obtain the measured blood coagulation evaluation result by evaluating a degree of blood coagulation based on the electrical characteristics of the blood sample; and an erythrocyte quantitative evaluation unit configured to determine a hematocrit value and/or a quantity of hemoglobin based on the electrical characteristics of the blood sample.

(11)

The blood state analysis device according to (10), wherein the blood coagulation evaluation unit is configured to evaluate the degree of the measured blood coagulation based on the electrical characteristics at a first frequency of the blood sample, and the erythrocyte quantitative evaluation unit is configured to determine the hematocrit value and/or the quantity of hemoglobin based on the electrical characteristics at a second frequency, which is different from the first frequency, of the blood sample.

(12)

A blood state analysis system comprising:

an electrical characteristics measuring device including a measuring unit configured to measure electrical characteristics of a blood sample comprising a plasma;

a blood state analysis device configured to analyze a state of the blood sample, wherein at least one reagent that is an anticoagulation treatment releasing agent, a coagulation activator, an anticoagulant, a platelet activator, an antiplatelet drug, or a combination thereof is present in the blood sample; and a correction unit configured to correct a measured blood coagulation evaluation result of the blood sample based on a relation between reference concentrations of the at least one reagent in plasma and reference blood coagulation evaluation results.

(13)

The blood state analysis system according to (12), further comprising: a server configured to store measurement results by the electrical characteristics measuring device and/or analysis results by the blood state analysis device.

(14)

The blood state analysis system according to (13), wherein the server is connected to the electrical characteristics measuring device and/or the blood state analysis device via a network.

(15)

A blood state analysis method that analyzes a state of a blood sample comprising a plasma and at least one reagent, the method comprising:

correcting a measured blood coagulation evaluation result of the blood sample based on a relation between reference concentrations of the at least one reagent in plasma and reference blood coagulation evaluation results, wherein the correcting comprises correcting the measured coagulation evaluation result to a corrected coagulation evaluation result that corresponds to a reference concentration of the at least one reagent in plasma that is substantially equal to a measured concentration of the at least one reagent in the plasma of the blood sample, and wherein the at least one reagent is an anticoagulation treatment releasing agent, a coagulation activator, an anticoagulant, a platelet activator, an antiplatelet drug, or a combination thereof.

(16)

A storage device comprising a blood state analysis program used to analyze a state of a blood sample having a plasma and at least one reagent, the program having computer-readable instructions that adapt a computer to:

correct a measured blood coagulation evaluation result of the blood sample based on a relation between reference concentrations of the at least one reagent in plasma and reference blood coagulation evaluation results, wherein the at least one reagent is an anticoagulation treatment releasing agent, a coagulation activator, an anticoagulant, a platelet activator, an antiplatelet drug, or a combination thereof.

(17)

A blood state analysis program used to analyze a state of a blood sample having a plasma and at least one reagent, the program having computer-readable instructions that adapt a computer to:

correct a measured blood coagulation evaluation result of the blood sample based on a relation between reference concentrations of the at least one reagent in plasma and reference blood coagulation evaluation results, wherein the at least one reagent is an anticoagulation treatment releasing agent, a coagulation activator, an anticoagulant, a platelet activator, an antiplatelet drug, or a combination thereof.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST

1 Blood state analysis device
11 Correction unit
12 Correlation detection unit
13 Blood coagulation evaluation unit
14 Plasma internal drug concentration calculation unit
15 Erythrocyte quantitative evaluation unit
16 Measuring unit
17 Storage unit
10 Blood state analysis system
101 Electric characteristics measuring device
102 Server
103 Display unit
104 User interface
I Correction process I
II Correlation detection process
III Blood coagulation evaluation process
IV Plasma internal drug concentration calculation process
V Erythrocyte quantitative evaluation process
VI Measuring process
VII Storage process

The invention claimed is:

1. A blood state analysis device that analyzes a state of a blood sample comprising a plasma and at least one reagent, the device comprising:
a correction unit configured to:
identify a hematocrit value and/or hemoglobin value of the blood sample;
identify a concentration of at least one reagent in plasma of the blood sample based at least in part on the hematocrit value and/or hemoglobin value, wherein the at least one reagent is an anticoagulation treatment releasing agent, a coagulation activator, an anticoagulant, a platelet activator, an antiplatelet drug, or a combination thereof and is present in the blood sample;
receive a measured coagulation result for the blood sample; and
correct the measured coagulation result to correspond to the concentration of the at least one reagent in the plasma of the blood sample.

2. The blood state analysis device according to claim 1, wherein the correction unit is further configured to correct the measured coagulation result based on previous measurements of blood coagulation as a function of concentration of the at least one reagent in blood plasma.

3. The blood state analysis device according to claim 1, wherein correcting the measured coagulation result comprises comparing the measured coagulation result to a reference blood coagulation evaluation result having a same concentration of the at least one reagent in plasma of a blood sample that was previously measured.

4. The blood state analysis device according to claim 3, further comprising: a correlation detection unit configured to determine a relation between concentrations of the at least one reagent in blood plasma and blood coagulation results for reference blood coagulation evaluation results.

5. The blood state analysis device according to claim 1, further comprising: a blood coagulation evaluation unit configured to obtain the measured coagulation result by evaluating a degree of blood coagulation based on electrical characteristics of the blood sample.

6. The blood state analysis device according to claim 1, further comprising: a plasma internal reagent concentration calculation unit configured to calculate the concentration of the at least one reagent present in the plasma of the blood sample based on the hematocrit value and/or the hemoglobin value of the blood sample.

7. The blood state analysis device according to claim 1, further comprising: an erythrocyte quantitative evaluation unit configured to determine the hematocrit value and/or the hemoglobin value of the blood sample based on electrical characteristics of the blood sample.

8. The blood state analysis device according to claim 7, further comprising: a plasma internal reagent concentration calculation unit configured to calculate the concentration of the at least one reagent present in the plasma of the blood sample based on the hematocrit value and/or the hemoglobin value obtained by the erythrocyte quantitative evaluation unit.

9. The blood state analysis device according to claim 1, further comprising a measuring unit configured to measure electrical characteristics of the blood sample.

10. The blood state analysis device according to claim 9, further comprising:
a blood coagulation evaluation unit configured to obtain the measured coagulation result by evaluating a degree of blood coagulation based on the electrical characteristics of the blood sample; and
an erythrocyte quantitative evaluation unit configured to determine the hematocrit value and/or the hemoglobin value based on the electrical characteristics of the blood sample.

11. The blood state analysis device according to claim 10, wherein
the blood coagulation evaluation unit is configured to evaluate the degree of the measured blood coagulation based on the electrical characteristics at a first frequency of the blood sample, and
the erythrocyte quantitative evaluation unit is configured to determine the hematocrit value and/or the hemoglobin based on the electrical characteristics at a second frequency, which is different from the first frequency, of the blood sample.

12. A blood state analysis method that analyzes a state of a blood sample comprising a plasma and at least one reagent, the method comprising:
identifying a hematocrit value and/or hemoglobin value of the blood sample;
identifying a concentration of at least one reagent in plasma of the blood sample based at least in part on the hematocrit value and/or hemoglobin value, wherein the at least one reagent is an anticoagulation treatment releasing agent, a coagulation activator, an anticoagulant, a platelet activator, an antiplatelet drug, or a combination thereof;
receiving a measured coagulation result for the blood sample; and
correcting the measured coagulation result to correspond to the concentration of the at least one reagent in the plasma of the blood sample.

13. The method of claim 12, wherein correcting the measured coagulation result comprises comparing the measured coagulation result to a reference blood coagulation evaluation result having a same concentration of the at least one reagent in plasma of a blood sample that was previously measured.

14. The method of claim 13, further comprising determining the relation between concentrations of the at least one reagent in blood plasma and blood coagulation to provide blood coagulation evaluation results.

15. The method of claim 12, further comprising obtaining the measured coagulation result by evaluating a degree of blood coagulation based on electrical characteristics of the blood sample.

16. The method of claim 12, further comprising calculating the concentration of the at least one reagent present in the plasma of the blood sample based on the hematocrit value and/or the hemoglobin value of the blood sample.

17. The method of claim 12, further comprising determining the hematocrit value and/or the hemoglobin value of the blood sample based on electrical characteristics of the blood sample.

18. The method of claim 17, further comprising:
determining, with an erythrocyte quantitative evaluation unit, the hematocrit value and/or the quantity of hemoglobin value based on electrical characteristics of the blood sample; and
calculating the concentration of the at least one reagent present in the plasma of the blood sample based on the hematocrit value and/or the quantity of hemoglobin obtained by the erythrocyte quantitative evaluation unit.

19. The method of claim 12, further comprising:
obtaining the measured coagulation result by evaluating a degree of blood coagulation based on first measured electrical characteristics of the blood sample; and
determining, with an erythrocyte quantitative evaluation unit, the hematocrit value and/or the quantity of hemoglobin value based on second measured electrical characteristics of the blood sample.

20. The method of claim 19, wherein
the first measured electrical characteristics are obtained at a first frequency and the second measured electrical characteristics are obtained at a second frequency, which is different from the first frequency.

* * * * *